United States Patent
Matsumoto et al.

(10) Patent No.: US 6,407,287 B2
(45) Date of Patent: Jun. 18, 2002

(54) METHOD FOR PRODUCTION OF ACRYLIC ACID

(75) Inventors: Yukihiro Matsumoto, Kobe; Takeshi Nishimura, Himeji; Kazuhiko Sakamoto, Himeji; Hidefumi Haramaki, Himeji, all of (JP)

(73) Assignee: Nippon Shokubai Co., Ltd. (JP)

( * ) Notice: Subject to any disclaimer, the term of this patent is extended or adjusted under 35 U.S.C. 154(b) by 0 days.

(21) Appl. No.: 09/800,705

(22) Filed: Mar. 7, 2001

(30) Foreign Application Priority Data

Mar. 8, 2000 (JP) ........................................ 2000-063252

(51) Int. Cl.⁷ ................ C07C 51/16; C07C 51/235; C07C 51/42
(52) U.S. Cl. .............. 562/532; 562/532; 562/542; 562/545; 562/521; 562/600
(58) Field of Search ............... 562/532, 542, 562/545, 521, 600

(56) References Cited

U.S. PATENT DOCUMENTS

| | | | |
|---|---|---|---|
| 5,315,037 A | * | 5/1994 | Sakamoto et al. |
| 5,785,821 A | | 7/1998 | Sakamoto et al. |
| 5,910,607 A | * | 6/1999 | Sakakura et al. |

FOREIGN PATENT DOCUMENTS

| | | |
|---|---|---|
| GB | A-2146636 | 4/1985 |
| JP | A-215266 | 3/1988 |
| JP | B-63-10691 | 3/1988 |

* cited by examiner

*Primary Examiner*—Jean F. Vollano
*Assistant Examiner*—Farhad Forohar
(74) *Attorney, Agent, or Firm*—Mathews, Collins, Shepherd & McKay, P.A.

(57) ABSTRACT

In a method for producing acrylic acid by the steps of a reaction of catalytic gas phase oxidation, absorbing the acrylic acid with an absorbent, and dehydrating the acrylic acid-containing aqueous solution, the method is characterized that the step of dehydration comprises adding and an azeotropic solvent, distilling the resultant mixture, and adjusting the acrylic acid concentration at the top of the column in the range of 0.06–0.80 wt. %, thereby preventing the bottoms of the azeotropic dehydration column from substantially containing the azeotropic solvent and water. As results, the acrylic acid is kept from forming a polymer in any of the distillation columns involved in the production, and effective utilization of acrylic acid.

9 Claims, 1 Drawing Sheet

METHOD FOR PRODUCTION OF ACRYLIC ACID

BACKGROUND OF THE INVENTION

1. Field of the Invention

This invention relates to a method for the production of acrylic acid, which method is characterized by preventing the bottoms of an azeotropic dehydration column from substantially containing a dehydrating solvent and water by causing the column top composition of the azeotropic dehydration column to have an acrylic acid concentration in the range of 0.06–0.80 wt. %.

2. Description of the Related Art

Acrylic acid is used in coating material, processed fibers, leather, and building material besides being utilized as a copolymer for acrylic fibers or as an adhesive agent in the form of emulsion. These applications have been placing a growing demand on the acrylic acid. Thus, the desirability of developing a process which allows use of an inexpensive raw material, permits expansion of production, and entails environmental pollution only sparingly has been finding popular recognition. The acrylic acid is generally produced by the reaction of catalytic gas phase oxidation of propylene, for example. The reaction of catalytic gas phase oxidation which yields acrylic acid as a target product, however, produces acrolein, aldehydes such as formaldehyde, compounds such as acetic acid which have lower boiling points than acrylic acid, and compounds such as acrylic acid dimer which have higher boiling points than acrylic acid as by-products thereof. This reaction, therefore, requires such steps as absorbing an acrylic acid-containing gas into an absorbent, removing contained aldehydes from the absorbent, depriving the absorbent of water, and then further separating low boiling substances and high boiling substances from the residue contained acrylic acid.

The acrylic acid itself, however, is chemically analogous with acetic acid particularly among other by-products mentioned above. These two compounds are not easily separated from each other because they possess similar physical and chemical properties such as vapor-liquid equilibrium. Thus, numerous suggestions have been made concerning a method for efficiently dehydrating and distilling an azeotropic agent from the acrylic acid-containing aqueous solution produced by the absorption of acrylic acid and further separating acetic acid therefrom by distillation.

The official gazette of JP-B-63-10,691, for example, discloses a method for producing purified acrylic acid by absorbing the gas formed by the catalytic gas phase oxidation of propylene and/or acrolein with molecular oxygen, supplying the resultant acrylic acid-containing aqueous solution to a dehydrating distillation column, then distilling this aqueous solution in the presence of an azeotropic solvent capable of forming an azeotropic mixture of water and acetic acid thereby expelling substantially the whole of the water and part of the acetic acid contained in the acrylic acid-containing aqueous solution, subsequently introducing the acrylic acid still retaining acetic acid therein as the bottoms of the column to an acetic acid separation column, distilling the persisting acetic acid in conjunction with the azeotropic solvent through the top of the acetic acid separation column, and meanwhile recovering the purified acrylic acid through the bottom of the column. The invention published in the official gazette mentioned above incidentally has been produced in view of the following problems. For example, the acetic acid cannot be effectively removed under the condition allowing no presence of the azeotropic solvent in the bottom part of the azeotropic dehydration column. An attempt to remove the acetic acid under the condition allowing no presence of an azeotropic solvent brings fatal defects such as suffering the acrylic acid to polymerize in the region from the middle part through the top of the distillation column and increasing the pressure drop of the column. For this reason, the practice of utilizing two columns, i.e. an azeotropic dehydration column and an acetic acid separation column, for the operation, using an azeotropic solvent in both the azeotropic dehydration column and the acetic acid separation column, expelling by distillation substantially the whole of water and part of acetic acid in the aqueous acrylic acid solution together with the azeotropic solvent mentioned above through the top of the azeotropic dehydration column, and subsequently subjecting in the acetic acid separation column the acetic acid and acrylic acid extracted through the bottom of the dehydration column to purification by the use of the azeotropic solvent mentioned above has been in vogue.

The official gazette of U.S. Pat. No. 5,910,607 discloses a method for the production of purified acrylic acid, which method comprises keeping the concentration of an azeotropic solvent in the range of 5–30 wt. % and the concentration of water not more than 0.5 wt. % in the bottoms of an azeotropic dehydration column, utilizing the azeotropic dehydration column and an acetic acid separation column for the operation, and setting the theoretical plate numbers of the columns each in the range of 5–20. Since acrylic acid is an unusually easily polymerizing substance, the distillation column after continuous operation tends to form a detestable polymer in the neighborhood of the bottom of the azeotropic dehydration column and in the neighborhood of the top of the acetic acid separation column. The invention published in this official gazette has been produced in view of this defective point. Specifically, by setting the concentration of the azeotropic solvent in the range of 5–30 wt. % and the concentration of water not more than 0.5 wt. %, preferably in the range of 0.3–0.05 wt. % in the bottoms of the azeotropic dehydration column, it is made possible to prevent the detestable polymerization of acrylic acid not only in the azeotropic dehydration column but also in the acetic acid separation column and allow the distillation column a lasting continuous operation. As a result, the method succeeds in removing inside the azeotropic dehydration column substantially the whole of water and part of acetic acid into the distillate emanating through the top of the column and obtaining an acrylic acid solution containing the acetic acid in the bottoms of the column and the azeotropic solvent having a concentration in the range of 5–30 wt. %. Particularly, the concentration of the azeotropic solvent in the bottoms of the azeotropic dehydration column is preferred to be as high as permissible from the viewpoint of preventing acrylic acid from polymerization. If the concentration is unduly high, however, the excess will be at an economic disadvantage in increasing the energy necessary for the separation of the azeotropic solvent in the acetic acid separation column. Further, in the acetic acid separation column, the concentration of the azeotropic solvent is preferred to be advantageous for the separation of acetic acid. Thus, the concentration of the azeotropic solvent has been limited to the range specified above. Incidentally, the invention of this official gazette sets the lower limit of the concentration of water in the bottoms of the azeotropic dehydration column at 0.05 wt. %. The reason for this lower limit is that if this concentration falls short of this lower limit, the shortage will be at a disadvantage in jeopardizing the prevention of polymerization by heightening the temperature of the bottom of the azeotropic dehydration column and further requiring the amount of the azeotropic solvent to be refluxed in the azeotropic dehydration column and, because of the consequent increase in the amount of acetic acid entrained in the distillate from the top of the column, inevitably inducing a decrease in the yield of the acetic acid to be recovered from the distillate of the acetic acid separation column.

The two-column type method of purification which comprises adding an azeotropic solvent to an acrylic acid-containing aqueous solution and subjecting this aqueous solution to azeotropic dehydration, then guiding the bottoms of the relevant azeotropic dehydration column to an acetic acid separation column, and purifying them therein through separation from acetic acid for the purpose of production of acrylic acid, however, requires the azeotropic solvent contained in the bottoms of the azeotropic dehydration column to be expelled by distillation in an acetic acid separation column operated at the subsequent step and necessitating energy for the separation and possibly entails difficulty in thoroughly removing the azeotropic solvent from the produced acrylic acid.

The unit cost of production can be lowered by rendering it possible to decrease the loss of the azeotropic solvent through the distillation column and the amount of the solvent to be used. Some of the substances which are discharged from the various distillation columns are reclaimable. When these effluents are simply discarded, the yield is lowered to the extent of rendering the production economically unfavorable and the discharged substances form a cause for environmental pollution.

Such being the case, the desirability of developing a method for the production of acrylic acid which operates satisfactorily with the existing equipment, allows the largest saving in the energy for purification, and prevents the reactants in the distillation columns from polymerization has been finding popular approval in the industry concerning the production of acrylic acid.

SUMMARY OF THE INVENTION

The present inventor, after making an elaborate study regarding the conditions for distillation to be used in an azeotropic dehydration column when an acrylic acid-containing aqueous solution is subjected to separation and purification by the use of at least two columns, i.e. the azeotropic dehydration column and an acetic acid separation column, has found that even when substantially the whole amount of an azeotropic solvent in the acrylic acid-containing aqueous solution is expelled by distillation from an azeotropic dehydration column into the distillate from the top of the column, the azeotropic dehydration column can be continuously operated for a long time without entailing polymerization of acrylic acid and that since the bottoms of the column do no longer contain the azeotropic solvent, the acetic acid separation column operated in the subsequent step obviates the necessity for separating the azeotropic solvent and excels in the efficiency of production and avoids inducing polymerization of acrylic acid. This invention has been perfected as a result. To be specific, the tasks imposed on this invention on account of the problems of the prior art mentioned above are accomplished by the following concept.

A method for the production of acrylic acid, comprising a step of subjecting propylene and/or acrolein to a reaction of catalytic gas phase oxidation, a step of absorbing the acrylic acid contained in the gas formed by the reaction of catalytic gas phase oxidation with an absorbent, and a step of dehydrating the acrylic acid-containing aqueous solution obtained by the step of absorption mentioned above, and characterized by the step of dehydration mentioned above adding and an azeotropic solvent capable of forming an azeotropic mixture with acetic acid and water and distilling the resultant mixture and adjusting the acrylic acid concentration at the top of the azeotropic dehydration column in the range of 0.06–0.80 wt. % thereby preventing the bottoms of the azeotropic dehydration column from substantially containing the azeotropic solvent and water.

In the method for the production of acrylic acid by the use of an azeotropic dehydration column and an acetic acid separation column, this invention can prevent acrylic acid from polymerization in the azeotropic dehydration column and the acetic acid separation column by merely adjusting the acetic acid concentration in the range of 0.06–0.80 wt. % with the tower top composition of the azeotropic dehydration column as a marker. Further, since acrylic acid and acetic acid are separated in the acetic acid separation column in the absence of the azeotropic solvent, the energy necessary for the distillation of the azeotropic solvent can be decreased Further, since the reactants in the acetic acid separation column contain an azeotropic solvent, the condenser attached to the column does not need to use chilled water as the cooling water therefore.

Further, this invention allows effective utilization of acrylic acid because it circulates partly or wholly the column top water phase and the column top distillate emanating from each of the azeotropic dehydration column and the acetic acid separation column to the acrylic acid absorption column and the azeotropic dehydration column and put them to use therein. It further allows the efficiency of the separation performed in the azeotropic dehydration column to be exalted by setting the site for feeding the column top distillate from the acetic acid separation column at a specific position in the azeotropic dehydration column.

DESCRIPTION OF THE PREFERRED EMBODIMENTS

The method of this invention for the production of acrylic acid comprises a step of subjecting propylene and/or acrolein to a reaction of catalytic gas phase oxidation, a step of absorbing the acrylic acid contained in the gas formed by the reaction of catalytic gas phase oxidation with an absorbent, and a step of dehydrating the acrylic acid-containing aqueous solution obtained by the step of absorption mentioned above, which method is characterized by the step of dehydration mentioned above adding and an azeotropic solvent capable of forming an azeotropic mixture with acetic acid and water to the column and distilling the resultant mixture thereby preventing the bottoms of the azeotropic dehydration column from substantially containing the azeotropic solvent and water and adjusting the acrylic acid concentration at the top of the azeotropic dehydration column in the range of 0.06–0.80 wt. %.

It has been heretofore customary to fulfill the purpose of preventing acrylic acid in the azeotropic dehydration column from polymerization as by selecting such conditions of distillation as the bottoms of the column mentioned above are allowed to contain the azeotropic solvent and then allowing also the separation column in the next step of separating acetic acid to contain the azeotropic solvent. It has been found, however, that by setting the acrylic acid concentration at the top of the azeotropic dehydration column in the range mentioned above, the azeotropic dehydration column is allowed a continuous operation for a long time without entailing formation of polymer of acrylic acid even when the treatment of distillation is carried out under the conditions of total absence of an azeotropic solvent in the bottoms of the azeotropic dehydration column. It has been further found that by thus preventing acrylic acid from polymerization, it is made possible to decrease the amount of the azeotropic solvent to be used, obviate the necessity for consuming energy in separating the azeotropic solvent in the produced acrylic acid, and attain further decrease in the amount of the azeotropic solvent persisting in the product. Now, this invention will be described further below.

First, this invention targets the acrylic acid thereof at the outcome of the reaction of catalytic gas phase oxidation of the raw material gas with a molecular oxygen-containing gas. To be specific, in the known reactor such as a shell-and-tube type reactor, the reaction of catalytic gas phase oxidation of propylene, propane, or acrolein is implemented by supplying a molecular oxygen-containing gas and an inert gas in their respectively specified amounts to the reactor in the presence of an oxidizing catalyst. For example, acrolein is formed by using propylene and acrylic acid is obtained by subjecting this acrolein further to the reaction of catalytic gas phase oxidation. The raw material gas, oxidizing catalyst, inert gas, and molecular oxygen-containing gas to be used and the reaction conditions for acrylic acid such as reaction temperature to be adopted may be similar to those involved in any of the known processes for acrylic acid.

The raw material gas which is composed of one or more raw material components selected from among propylene, propane, and acrolein and used at a concentration in the range of 1–15 vol. %, molecular oxygen intended to effect the reaction of oxidation and used in an amount in the range of 1–3 times the amount of the raw material component, and an inert gas such as carbon dioxide or steam used in an amount accounting for the remainder is supplied to the reactor. Though the reactor for carrying out the reaction of catalytic gas phase oxidation does not need to be particularly discriminated, the shell-and-tube type reactor can be advantageously used in respect that it excels in the efficiency of reaction.

For the production of acrylic acid by the two-stage reaction of catalytic gas phase oxidation of a propylene-containing gas, for example, the oxidizing catalyst which is generally used in the production of acrolein by the reaction of catalytic gas phase oxidation of the raw material containing propylene can be used as the former-stage catalyst. The latter-stage catalyst does not need to be particularly discriminated. For the purpose of producing acrylic acid by the gas phase oxidation of the reaction gas mainly containing acrolein and obtained by the former stage of the two-stage method for catalytic gas phase oxidation, the oxidizing catalyst which is generally used can be adopted.

As the former-stage catalyst, a catalyst which is represented by the general formula, $Mo_a$—$Bi_b$—$Fe_c$—$A_d$—$B_e$—$C_f$—$D_g$—$O_x$ (wherein Mo, Bi, and Fe stand respectively for molybdenum, bismuth, and iron, A for at least one element selected from the group consisting of nickel and cobalt, B for at least one element selected from the group consisting of alkali metals and thallium, C for at least one element selected from the group consisting of phosphorus, niobium, manganese, cerium, tellurium, tungsten, antimony, and lead, D for at least one element selected from the group consisting of silicon, aluminum, zirconium, and titanium, O for oxygen, a, b, c, d, e, f, g, and x respectively for the atomic ratios of Mo, Bi, Fe, A, B, C, D, and O, which fall respectively in the ranges of b=0.1–10, c=0.1–10, d=2–20, e=0.001–5, f=0–5, and g=0–30 when a=12 is fixed, and x for the value to be fixed by the states of oxidation of the relevant elements) may be cited.

Then, as the latter-stage catalyst, a catalyst which is represented by the general formula, $Mo_a$—$V_b$—$W_c$—$Cu_d$—$A_e$—$B_f$—$C_g$—$O_x$ (wherein Mo stands for molybdenum, V for vanadium, W for tungsten, Cu for copper, A for at least one element selected from the group consisting of antimony, bismuth, tin, niobium, cobalt, iron, nickel, and chromium, B for at least one element selected from the group consisting of alkali metals, alkaline earth metals, and thallium, C for at least one element selected from the group consisting of silicon, aluminum, zirconium, and cerium, O for oxygen, a, b, c, d, e, f, g, and x respectively for the atomic ratios. of Mo, V, W, Cu, A, B, C, and O. which fall respectively in the ranges of b=2–14, c=0–12, d=0.1–5, e=0–5, f=0–5, and g=0–20 when a=12 is fixed, and x for value to be fixed by the states of oxidation of the relevant elements) may be cited.

The conditions for the preparation of the catalyst to be used in this invention excepting the firing temperature and the raw materials to be mixed and used for forming the catalyst excepting molybdenum oxide do not need to be particularly discriminated. The conditions and the raw materials which are in popular use may be adopted. The shape of the catalyst does not need to be particularly discriminated. Spheres, cylinders, tubes, and the like may be used. As the method of forming, deposit molding, extrusion molding, tablet molding, and the like may be used. Further, the form which has such catalytic substance deposited on a refractory carrier is useful.

The step for absorbing acrylic acid with an absorption means a step for absorbing acrylic acid contained in the gas obtained by the step of reaction with an absorbent. The conditions for the absorption including the composition of the reaction gas, the composition of the absorbent, and the temperature of absorption may be selected from among those of the known processes for the absorption of acrylic acid. Incidentally, the gas formed by the reaction of oxidation possibly contains unreacted acrolein. For this reason, the acrylic acid-containing aqueous solution mentioned above is preferred to be obtained after the unreacted acrolein has been removed by distillation or stripping, for example.

At the step of absorption, the acrylic acid-containing gas is introduced into the absorption column and the absorbent for absorbing acrylic acid is meanwhile introduced into the column through the upper part thereof and brought into counterflow contact with the gas just mentioned to effect absorption of acrylic acid. The mixed gas guided to the acrylic acid absorption column generally contain acrylic acid, acetic acid, and water in amounts falling respectively in the ranges of 10–20 wt. %, 0.2–1.0 wt. %, and 5–15 wt. %.

Incidentally, as the absorption column, any of the known absorption columns such as plate column, packed column, wetted-wall column, and spray column may be used. Among other absorption columns, the plate column or the packed column is generally used particularly advantageously. In the case of the packed column, a packing having a large surface area and possessing perviousness to gas is regularly or irregularly packed in the interior of the column. On the surface of each of the packed beds filled with the packing, the gas-liquid contact is carried out.

As the absorbent to be supplied, the known solvents such as water and organic acid-containing water may be cited. These absorbents may be used either singly or in the form of a mixture of two or more members. One of the absorbents to be used in the absorption column is composed of 0.1–5.0 wt. % of acrylic acid, 0.1–10 wt. % of acetic acid, and 80–99.8 wt. % of water.

The absorbent is preferred, for the sake of preventing such polymerizing substances as acrylic acid from polymerization, to add suitably any of known polymerization inhibitors such as hydroquinone monomethyl ether, manganese acetate, nitrosophenol, cupferron, N-oxyl compounds, copper dibutyl thiocarbamate, phenothiazine, and hydroquinone.

The absorbent is put to use after it has been adjusted to the composition specified above. The water phase in the storage tank attached to the azeotropic dehydration column may be circulated as the absorbent for acrylic acid to the acrylic acid absorption column and used therein as will be described specifically below.

The operating condition in the absorption column are decided by such factors as the pressure, temperature, composition of absorption liquid, and amount of absorption liquid. A low temperature and a large amount of absorption liquid are favorable conditions. Since these conditions are affected by the subsequent steps, it is commendable to set appropriate conditions by taking into account such requirements as mentioned above.

In this invention, the acrylic acid concentration in the acrylic acid-containing aqueous solution to be supplied to the azeotropic dehydration column is properly in the range of 55–80 wt. %, preferably in the range of 60–75 wt. %, and particularly in the range of 65–75 wt. %. The conditions for the operation of the absorption column, therefore, are preferred to be set so as to ensure production of such an acrylic acid-containing aqueous solution as mentioned above. Acrylic acid is most liable to polymerize when the ratio of acrylic acid to water is about 50:50. When the acrylic acid concentration in the acrylic acid-containing aqueous solution falls short of 55 wt. %, therefore, the acrylic acid is liable to polymerize in the azeotropic dehydration column used at the subsequent step. The amount of the azeotropic solvent to be used varies with the amount of water. The acrylic acid concentration, therefore, is preferred to exceed 55 wt. % even for the purpose of decreasing the amount of the azeotropic solvent and consequently decreasing the energy for the distillation. If the acrylic acid concentration exceeds 80 wt. %, the excess will be at a disadvantage in extremely lowering the efficiency of absorption in the absorption column. The concentration of acetic acid in the bottoms of this absorption column is preferably in the range of 0.1–4 wt. %, more preferably in the range of 0.2–3 wt. %. The acetic acid concentration is preferred to be as low as permissible. If it exceeds 4 wt. %, the excess will be at a disadvantage in suffering acetic acid to persist in the bottom of the azeotropic dehydration column. Then, the water concentration is generally in the range of 20–45 wt. %.

This invention requires this acrylic acid-containing aqueous solution to be guided to the azeotropic dehydration column and subjected therein to azeotropic distillation with the azeotropic solvent supplied separately thereto.

Here, as the azeotropic dehydration column, any of the known columns such as a plate column, a packed column, a wetted-wall column, and a spray column may be used. As such an azeotropic dehydration column, the plate column or the packed column, whichever better fits the occasion, is generally used advantageously.

As concrete examples of the azeotropic solvent to be used for this invention, the solvent containing at least one member selected from the group consisting of heptane, dimethyl cyclohexane, ethyl cyclohexane, toluene, ethyl benzene, chlorobenzene, xylene, and mixtures thereof;

the solvent containing at least one member selected from the group consisting of diethyl ketone, diisopropyl ketone, methylpropyl ketone, methylisobutyl ketone, methyl-t-butyl ketone, n-propyl acetate, n-butyl acetate, ethyl acrylate, methyl methacrylate, ethyl methacrylate, vinyl acrylate, n-propyl acrylate, allyl acetate, isopropenyl acetate, vinyl propionate, propyl propionate, methyl crotonate, methyl valerate, ethyl butyrate, dibutyl ether, and mixtures thereof; and the mixed solvent between the solvent containing at least one member selected from the group consisting of heptane, dimethyl cyclohexane, ethyl cyclohexane, toluene, ethyl benzene, chlorobenzene, xylene, and mixtures thereof and the solvent containing at least one member selected from the group consisting of diethyl ketone, diisopropyl ketone, methylpropyl ketone, methylisobutyl ketone, methyl-t-butyl ketone, n-propyl acetate, n-butyl acetate, ethyl acrylate, methyl methacrylate, ethyl methacrylate, vinyl acrylate, n-propyl acrylate, alloy acetate, isopropenyl acetate, vinyl propionate, propyl propionate, methyl crotonate, methyl valerate, ethyl butyrate, dibutyl ether, and mixtures thereof may be cited.

As more preferable azeotropic solvents, the solvent containing at least one member selected from the group consisting of heptane, toluene, ethyl benzene, xylene, and mixtures thereof; the mixed solvent between the solvent just mentioned and at least one member selected from the group containing of ethyl acrylate, methyl methacrylate, ethyl methacrylate or the solvent containing at least one member selected from the group consisting of ethyl methacrylate, diisopropyl ketone, n-propyl acrylate, n-butyl acetate, and mixtures thereof may be cited.

The amount of the azeotropic solvent to be used herein cannot be uniquely defined because it is fixed by the water content in the bottoms of the absorption column to be supplied to the azeotropic dehydration column and the kind of the azeotropic solvent to be used. The azeotropic solvent, however, can be used at the known rate which is used for the purpose of an azeotropic treatment. Though the amount of the azeotropic distillation is preferred to be as large as permissible particularly from the viewpoint of preventing acrylic acid from polymerization, the use of this solvent in an unduly large amount brings the disadvantage of necessitating a large volume of energy for distillation.

In this invention, the acrylic acid concentration at the top of the azeotropic dehydration column is adjusted in the range of 0.06–0.80 wt. %. This invention is characterized by preventing the bottoms of the azeotropic dehydration column from substantially containing water and an azeotropic solvent. By fulfilling this requirement, this invention is enabled to decrease the amount of the azeotropic solvent to be used and dispense with the work of removing the azeotropic solvent in the acetic acid separation column. As a result of the elaborate study performed on the conditions which are capable of preventing the bottoms from containing the azeotropic solvent and water, it has been found that the prevention aimed at can be easily accomplished by adjusting the acrylic acid concentration at the top of the azeotropic dehydration column in the range of 0.06–0.80 wt. %, preferably in the range of 0.08–0.60 wt. %, and particularly in the range of 0.10–0.50 wt. %. Acrylic acid has a boiling point of 141° C. The azeotropic solvent mentioned above, water, and acetic acid jointly forms an azeotropic composition, which has a lower boiling point than acrylic acid. By setting such conditions as the acrylic acid is expelled by distillation, if only minutely, through the top of the column, therefore, it is made possible to attain substantial expulsion by distillation of water and the azeotropic solvent through the top of the column and consequently prevent the bottoms from containing water and the azeotropic solvent. The acrylic acid-containing aqueous solution which is supplied contains aldehyde and other low boiling substances besides acrylic acid and acetic acid. By setting the acrylic acid concentration at the top of the column at or above 0.06 wt. %, however, it is made possible to expel the low boiling substances including aldehyde out of the column by distillation. As a result, the polymerization of acrylic acid owing to the inclusion of such low boiling substances can be prevented. Meanwhile, by setting the concentration within 0.80 wt. %, it is made possible to control the acrylic acid concentration and prevent the acrylic acid from polymerization.

It has been heretofore customary to prevent the polymerization of acrylic acid by increasing the amount of the azeotropic solvent to be supplied to the azeotropic dehydration column and heightening the concentration of the azeotropic solvent in the column. The measure has necessitated separation of the azeotropic solvent at the subsequent step. This invention is enabled to attain the removal of the azeotropic solvent from the bottoms substantially wholly and obviate the necessity for incorporating a step for the separation of the azeotropic solvent by expelling the acrylic acid from the top of the column in a larger amount than ever. Since the low boiling substances including aldehyde can be also expelled by distillation as described above, the generation of a polymer of acrylic acid in the azeotropic dehydration column can be prevented effectively. The expression "preventing the bottoms of the azeotropic dehydration column from substantially containing the azeotropic solvent and water" means that the concentrations of both the substance are lowered to below 0.05 wt. %, preferably to below 0.04 wt. %, and more preferably to below 0.02 wt. %.

Incidentally, the adjustment of the acrylic acid concentration at the top of the azeotropic dehydration column in the range of 0.06–0.80 wt. % can be attained by adjusting the distillation temperature and the inner pressure of the azeotropic dehydration column and the ref lux ratio from the condenser attached to the azeotropic dehydration column. Though the condensate which has been formed by the condensation of the top gas in the condenser contains the components other than the high boiling substances as described above, it is separated into an organic phase formed substantially wholly of the azeotropic solvent (hereinafter referred to the "azeotropic solvent-containing phase") and a water phase containing other components. The act of refluxing the azeotropic solvent-containing phase to the azeotropic dehydration column, therefore, proves advantageous in respect that it allows effective utilization of the azeotropic solvent. The water phase can be reclaimed as the absorbent for the acrylic acid absorption column. Specifically, though this invention has such preconditions as expelling the whole of the azeotropic solvent through the top of the azeotropic dehydration column and consequently causing a small amount of acrylic acid to be expelled by distillation through the top of the column, it is enabled to exalt the yield of production by circulating the azeotropic solvent-containing phase and the water phase in the produced condensate respectively to the azeotropic dehydration column and the absorption column and putting them to use and consequently attaining effective utilization of the azeotropic solvent and acrylic acid contained in the circulated phases. The reflux ratio of the azeotropic solvent-containing phase is properly in the range of 0.5–10, and more preferably in the range of 2–9. So long as the reflux ratio is in this range, the separation of acetic acid is attained fully satisfactorily.

The acetic acid concentration of the bottoms of the azeotropic dehydration column is set properly in the range of 0.02–3 wt. %, preferably in the range of 0.1–2 wt. %, and particularly in the range of 0.2–1.5 wt. %. Though the acetic acid concentration is preferred to be as low as permissible from the viewpoint of the production of purified acrylic acid, the conditions for lowering this concentration below 0.02 wt. % are at a disadvantage in adding to the theoretical plate number of the dehydration column and necessitating an increase in the amount of the solvent. They further bring the disadvantage of lowering the operating pressure and consequently necessitating an addition to the heat transfer surface area of the condenser and increasing the steam flow rte supplied to the reboiler as well. Conversely, if this concentration exceeds 3 wt. %, the excess will be at a disadvantage in rendering it difficult to remove acetic acid exclusively by the two columns, i.e. the azeotropic dehydration column and the acetic acid separation column. According to this invention, even in the two-column type plant including an acetic acid separation column, for example, the steam flow rate supplied to the reboiler required to be purified is small as compared with the amount involved in the case of the one-column plant which possesses no acetic acid separation column and effects the purification solely with the azeotropic dehydration column. The two-column plant, in spite of the inclusion of the acetic acid separation column, proves economical as compared with the one-column plant in consideration of the total amount of the energy required for the purification and the factors of equipment such as, for example, the theoretical plate number of the azeotropic dehydration column.

Incidentally, the temperature of the bottoms of the azeotropic dehydration column is preferred to be not higher than 120° C. for the purpose of preventing acrylic acid from polymerization. Since the azeotropic dehydration column is generally operated under a reduced pressure, the control of the temperature of the bottoms is enabled by regulating the pressure at the top of the column. The azeotropic dehydration column is preferred to have a theoretical plate number in the range of 10–20. The dehydration column is generally operated under column top pressure in the range of 20–200 hPa. Heretofore, the condition that substantially the whole amount of water be removed for the purpose of keeping the temperature of the bottoms from rising and consequently preventing acrylic acid from polymerization has not been adopted at times. According to this invention, the polymerization of acrylic acid will not occur even when the water is substantially removed from the bottoms. Though the reason for this difference remains yet to be elucidated, it may be logically explained by a supposition that the low boiling substances including aldehyde are expelled by distillation as described above.

It is commendable for the sake of preventing acrylic acid from detestable polymerization to add suitably any of known polymerization inhibitors such as hydroquinone monomethyl ether, manganese acetate, nitrosophenol, cupferron, N-oxy compounds, copper dibutyl thiocarbamate, phenothiazine, and hydroquinone to the azeotropic dehydration column. Such a polymerization inhibitor may be supplied in the form of a solution additionally containing at least one member selected from among acrylic acid, azeotropic solvent, and water to the top and/or the middle part of the column. For the same purpose, a molecular oxygen-containing gas may be blown into the column through the bottom thereof.

The bottoms of the azeotropic dehydration column thus obtained contain acrylic acid at a concentration in the range of 92–99 wt. % and acetic acid at a concentration in the range of 0.02–3 wt. %.

In this invention, acetic acid can be separated from the bottoms of the azeotropic dehydration column and acrylic acid can be extracted in a purified state in the acetic acid separation column.

Here, as the acetic acid separation column, any of the known columns such as a plate column, a packed column, a wetted-wall column, and a spray column can be used. As the acetic acid separation column, similarly to the azeotropic dehydration column, the plate column or the packed column, whichever better fits the occasion, generally proves advantageous. It is filled with a packing or plates.

The distillation in the acetic acid separation column may be performed under any of the known conditions which fit the distillation. For example, it is carried out under a column top pressure in the range of 20–100 hPa at a column bottom temperature of not higher than 100° C. It has been heretofore customary to add an azeotropic solvent to the acetic acid separation column for the purpose of preventing the acetic acid separation column from inducing polymerization or allow the azeotropic solvent to persist in the bottoms of the azeotropic dehydration column. Since this invention is enabled to expel by distillation easily polymerizing compounds including aldehyde by adjusting the acrylic acid concentration in the column top gas of the azeotropic dehydration column in the range of 0.06–0.80 wt. %, it is capable of preventing the acrylic acid in the bottoms from polymerization and also preventing the acrylic acid in the subsequent acetic acid separation column from yielding to polymerization. Furthermore, the distillation in the acetic acid separation column can be carried out under the same conditions as those heretofore adopted for the purpose of distillation. Further in this invention, the bottoms of the azeotropic dehydration column which is supplied to the acetic acid separation do not contain an azeotropic solvent, the condensate of gas produced in the condenser attached to the column has a high temperature and does not require chilled water as a cooling water. The energy required for distilling the azeotropic solvent may be decreased.

The acetic acid separation column, similarly to the azeotropic dehydration column, is preferred for the sake of preventing acrylic acid from yielding to detestable polymerization to add suitably any of the known polymerization inhibirors such as hydroquinone monomethyl ether, manganese acetate, nitrosophenol, cupferron, N-oxyl compounds, copper dibutyl thiocarbamate, phenothiazine, and hydroquinone. Such a polymerization inhibitor can be supplied in the form of an acrylic acid-containing aqueous solution to the top and/or the middle part of the column. For the same purpose, a molecular oxygen-containing gas can be blown into the column through the bottom thereof.

This invention allows the condensate of the distillate of the gas emanating through the top of the azeotropic dehydration column to be circulated to the absorption column and the azeotropic column and put to use therein. In addition to this circulating use or independently thereof, the distillate gas containing acrylic acid may be obtained through the top of the acetic acid separation column and condensed and the resultant acrylic acid-containing condensate may be supplied at least partly to the azeotropic dehydration column. This partial recirculation of the acrylic acid-containing condensate enables acrylic acid to be further utilized effectively. The condensate generally contain acrylic acid at a concentration in the range of 90–99 wt. % and acetic acid at a concentration in the range of 1–10 wt. %. In this circulation to the azeotropic dehydration column, the position for supplying the condensate to the azeotropic dehydration column is preferred to be on the same level as or lower than the inlet for supply of the acrylic acid-containing condensate to the azeotropic dehydration column. Under the conditions used by this invention in the azeotropic dehydration column, acrylic acid concentration in the column rises higher as it goes down from the position for supplying the condensate, and the condensate introduced to the column contains acrylic acid higher than the acrylic acid-containing aqueous solution. So, the position for supplying the condensate to the azeotropic dehydration column is fixed at the same level as or lower than the position for supply of the acrylic acid-containing aqueous solution. As a result, the solution intended for purification is enabled to be supplied to the distillation column at the position approximating most closely to the composition in the column, the efficiency of separation in the azeotropic dehydration column will not be lowered.

EXAMPLES

Now, this invention will be described more specifically below with reference to working examples.

Example of Production of Catalyst

In 150 liters of purified water which was kept heated and stirred, 100 kg of ammoniummolybdate and 6.3 kg of ammonium paratungstate were dissolved. To the resultant solution, an aqueous nitrate solution prepared by dissolving 68.7 kg of cobalt nitrate in 100 liters of purified water, 19 kg of ferric nitrate in 30 liters of purified water, and 22.9 kg of bismuth nitrate in 30 liters of purified water additionally incorporating therein 6 liters of concentrated nitric acid and then mixing the resultant solutions was added dropwise. Subsequently, a solution obtained by dissolving 14.2 kg of an aqueous 20 wt. % silica sol solution and 0.29 kg of potassium nitrate in 15 liters of purified water was added thereto. The suspension thus obtained was heated and stirred till evaporation to dryness and then dried and pulverized. The resultant powder was molded in the shape of a cylinder 5 mm in diameter and fired under a current of air at 460° C. for six hours to obtain a catalyst.

Example 1

Figure 1:
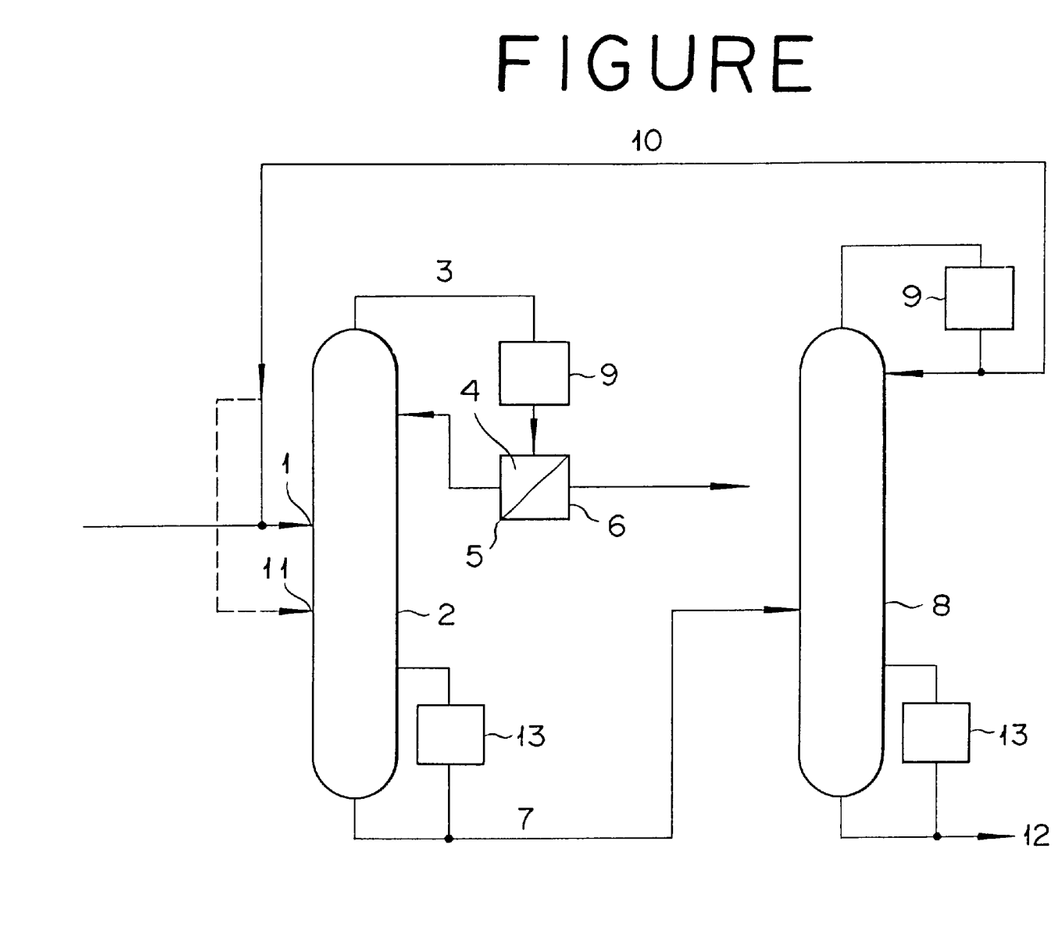
FIG. 1 is a schematic diagram illustrating the process for the production of acrylic acid according to this invention.

Acrylic acid was produced in accordance with the process diagram illustrated in FIG. 1. With reference to FIG. 1, 1 stands for an inlet for supply of an acrylic acid-containing aqueous solution, 2 for an azeotropic dehydration column, 3 for a gas line at the top of the azeotropic dehydration column, 4 for a condenser reflux liquid (azeotropic solvent-containing phase), 5 for an oil-water separation vessel, 6 for a water phase, 7 for the bottoms line of the azeotropic dehydration column, 8 for an acetic acid separation column, 9 for a condenser, 10 for a column top line of the acetic acid separation column, 11 for an inlet for supplying the column top liquid to the acetic acid separation column, 12 for a line for the produced acrylic acid, and 13 for a reboiler.

First, a reaction tube was filled with the catalyst (composed of Mo, Bi, Fe, Co, W, Si, and K at respective molar ratios of 12:1.0:1:5:0.5:1:0.06) obtained in the example of production cited above and intended for use in the formation of acrolein mainly from propylene and a raw material gas composed of 7 vol. % of propylene, 12 vol. % of oxygen, 7 vol. % of water, and 74 vol. % of an inert gas was supplied to the filled reaction tube at a feed rate of 169 Nm$^3$ per hour. The reaction gas obtained from this reactor was composed of 5.8 vol. % of acrylic acid, 14.8 vol. % of water, 76.3 vol. % of an inert gas, and a total of 3.1 vol. % of terephthalic acid, formaldehyde, and maleic acid.

The acrylic acid-containing gas was supplied to an absorption column at a temperature of 150° C. Hydroquinone was added as a polymerization inhibitor to the column through the top thereof. This absorption column was operated under a column top absolute pressure of 110 kPa to absorb acrylic acid. The bottoms of the absorption column were composed of 63.8 wt. % of acrylic acid, 2.5 wt. % of acetic acid, 32.5 wt. % of water, and the balance of maleic acid, acetoaldehyde, acrolein, etc. plus 200 ppm of hydroquinone.

Then, part of the acrylic acid-containing aqueous solution (the bottoms of the absorption column) was supplied to the azeotropic dehydration column (2) illustrated in FIG. 1 through the inlet for supply of the acrylic acid-containing aqueous solution (1).

Subsequently, the bottoms of the absorption column were supplied at a rate of 10 kg/h to the 18th plate from above of the azeotropic dehydration column (2) provided with 40 sieve trays. To the azeotropic dehydration column (2), part of the column top liquid (acrylic acid-containing condensate) from the acetic acid separation column (8) which continued to the dehydration column (2) at a rate of 1.6 kg/h similarly through the inlet (11) at the 18th plate for supply of the column top liquid. In the azeotropic dehydration column (2), the column top liquid was distilled under a column top absolute pressure of 187 hPa at the 15th plate temperature of 65° C. by using toluene as an azeotropic solvent. The distillate emanating from the column top was condensed in the condenser (9) attached to the column top gas line (3) of the azeotropic dehydration column. The resultant condensate was separated into two phases. When the toluene phase (azeotropic solvent-containing phase) (4) was wholly refluxed at a rate of 19.5 kg/h, the acrylic acid concentration in the column top gas of the azeotropic dehydration column was 0.2 wt. %. The toluene phase (4) incorporated phenothiazine as a polymerization inhibitor till a concentration of 150 ppm and molecular oxygen was supplied thereto through the bottom at a rate of 40 N liters/h to effect distillation. The acetic acid concentration of the bottoms was 0.8 wt. %. The bottoms contained neither toluene nor water. The bottoms were obtained at a rate of 8.1 kg/h.

Subsequently, the bottoms of the azeotropic dehydration column were supplied to the 18th plate from the top of the acetic acid separation column (8) provided with 35 sieve trays. This column was operated under a column top absolute pressure of 53 hPa by supplying molecular oxygen thereto through the bottom thereof at a rate of 15 N liters/h and using a reflux ratio of 2.0. Through the top of the column, the acrylic acid-containing condensate containing 4 wt. % of acetic acid was obtained at a rate of 4.8 kg/h and condensed by being cooled with a condenser attached thereto. Of the resultant condensate, the portion of 1.6 kgh was returned to the azeotropic dehydration column (2) in the manner described above. The reflux liquid from the condenser (9) additionally incorporated therein hydroquinone as a polymerization inhibitor till a concentration of 100 ppm. Through the bottom of the column, not more than 500 ppm of acrylic acid was obtained at a rate of 6.5 kg/h.

The steam flow rate for the reboiler of the azeotropic dehydration column (2) was 10.2 kg/h and that of the acetic acid separation column was 1.5 kg/h. The total steam flow rate for the reboiler required for the operation was 11.7 kg/h.

When the azeotropic dehydration column (2) and the acetic acid separation column (8) were continuously operated for 14 days under the conditions mentioned above and their interiors were inspected thereafter, the 18th plate of the azeotropic dehydration column was observed to carry a deposit thereon slightly but show absolutely no sign of the formation of a polymer.

Comparative Example 1

When the same acrylic acid-containing aqueous solution, azeotropic dehydration column, and acetic acid separation column as used in Example 1 were adopted and the temperature of the 15th plate of the azeotropic dehydration column was set at 60° C., the acrylic acid concentration of the gas emanating through the top of the azeotropic dehydration column (2) was found to be 0.05 wt. %. The bottoms were found to have an acetic acid concentration of 1.7 wt. % and contain neither toluene nor water. The bottoms were obtained at a rate of 6.5 kg/h.

When the amount of the distillate to be obtained from the acetic acid separation column (8) was altered so as to change the acetic acid concentration of the bottoms to not more than 500 ppm, the distillate was obtained at a rate of 5 kg/h. This distillate was supplied to the azeotropic dehydration column (2) and treated therein under entirely the same conditions as in Example 1 excepting the change of the reflux ratio to 1.0.

The steam flow rate for the reboiler obtained from the azeotropic dehydration column was 9.8 kg/h and that from the acetic acid separation column was 3.1 kg/h and the total steam flow rate for the reboiler required for the operation was 12.9 kg/h.

The operation of the azeotropic dehydration column (2) was discontinued when the pressure in the bottom of the azeotropic dehydration column (2) abruptly rose after 5 days of continued operation. When the interior of the column was then inspected, the 18th through 30th plates of the column were found to be covered with 2.5 liters of deposited polymer.

Comparative Example 2

When the same acrylic acid-containing aqueous solution, azeotropic dehydration column, and acetic acid separation column as used in Example 1 were adopted and the temperature of the 15th plate of the azeotropic dehydration column was set at 70° C., the acrylic acid concentration of the gas emanating through the top of the azeotropic dehydration column (2) was found to be 0.9 wt. %. The bottoms were found to have an acetic acid concentration of 0.3 wt. % and contain neither toluene nor water. The bottoms were obtained at a rate of 6.8 kg/h.

When the amount of the distillate to be obtained from the acetic acid separation column (8) was altered so as to change the acetic acid concentration of the bottoms to not more than 500 ppm, the distillate was obtained at a rate of 0.5 kg/h. This distillate was supplied to the azeotropic dehydration column (2) and operated therein under entirely the same conditions as in Example 1 excepting the change of the reflux ratio to 5.0.

The steam flow rate for the reboiler obtained from the azeotropic dehydration column was 10.6 kg/h and that from the acetic acid separation column was 1.0 kg/h and the total steam flow rate for the reboiler required for the operation was 11.6 kg/h.

The operation of the azeotropic dehydration column (2) was discontinued when the pressure in the bottom of the azeotropic dehydration column (2) abruptly rose after 7 days of continued operation. When the interior of the column was then inspected, the 6th through 18th plates of the column were found to be covered with 2.0 liters of deposited polymer.

Example 2

Acrylic acid was produced by following the process diagram illustrated in FIG. 1.

When the acrylic acid-containing aqueous solution of Example 1 was prepared with water and hydroquinone, the bottoms of the absorption column consequently obtained were found to be composed of 49.0 wt. % of acrylic acid, 1.9 wt. % of acetic acid, 48.1 wt. % of water, and the balance of maleic acid, acetaldehyde, acrolein, etc. plus 200 ppm of hydroquinone.

The bottom of the absorption column were supplied at a rate of 7 kg/h through the inlet for acrylic acid-containing aqueous solution (1) at the 18th plate from above of the azeotropic dehydration column (2) provided with 40 sieve trays. To the azeotropic dehydration column (2), part of the column top liquid from the acetic acid separation column (8) which continued to the dehydration column (2) was supplied similarly through the inlet at the 18th plate.

In the azeotropic dehydration column (2), the column top liquid was distilled under a column top absolute pressure of 187 hPa at the 15th plate temperature of 65° C. and was condensed in the condenser (9) attached thereto. The resultant condensate was separated into two phases. When the toluene phase (4) was wholly refluxed at a rate of 19.5 kg/h, the acrylic acid concentration in the column top gas of the azeotropic dehydration column was 0.3 wt. %. To the refluxed liquid (4), phenothiazine was added as a polymerization inhibitor till a concentration of 150 ppm and molecular oxygen was supplied thereto through the bottom at a rate of 40 N liters/h to effect distillation. The bottoms of the column were found to contain neither toluenenor water. These bottoms were obtained at a rate of 3.8 kg/h.

Subsequently, the bottoms of the azeotropic dehydration column (2) mentioned above were supplied to the 15th plate from the top of the acetic acid separation column (8) provided with 35 sieve trays. This column was operated under a column top absolute pressure of 53 hPa by supplying molecular oxygen thereto through the bottom thereof at a rate of 15 N liters/h and using a reflux ratio of 6.0. Through the top of the column, acrylic acid containing 4 wt. % of acetic acid was expelled by distillation at a rate of 0.4 kg/h. This acrylic acid was returned to the azeotropic dehydration column (2) in the manner described above. The reflux liquid of the condenser (9) additionally incorporated therein hydroquinone as a polymerization inhibitor till a concentration of 100 ppm. Through the bottom of the column, acrylic acid containing acetic acid in a concentration of not more than 500 ppm was obtained at a rate of 3.4 kg/h.

The steam flow rate for the reboiler of the azeotropic dehydration column was 10.4 kg/h and that of the acetic acid separation column was 0.9 kg/h. The total steam flow rate for the reboiler required for the operation was 11.3 kg/h.

When the azeotropic dehydration column (2) and the acetic acid separation column (8) were continuously operated for 14 days under the conditions mentioned above and their interiors were inspected thereafter, the 18th through 25th plates of the azeotropic dehydration column were observed to carry thereon 0.1 liter of polymer.

Example 3

Acrylic acid was produced by following the procedure of Example 1 while supplying part of the column top liquid of the acetic acid separation column to the 35th plate of the azeotropic dehydration column and changing the reflux ratio of the acetic acid separation column.

As a result, when the bottoms of the acetic acid separation column were adjusted so as to lower the acetic acid concentration thereof to not more than 500 ppm, the reflux ratio of the condensate of acrylic acid was found to be 1.6. As respects the condition of deposition on the azeotropic dehydration column, the 18th plate was found to carry thereon a slight amount of deposit but show absolutely no sign of a polymer. The steam flow rate for the reboiler of the azeotropic dehydration column was 10.2 kg/h and that of the acetic acid separation column was 1.3 kg/h and the total steam flow rate for the reboiler required for the operation was 11.5 kg/h.

Example 4

Acrylic acid was produced by following the process diagram illustrated in FIG. 1.

First, the same acrylic acid-containing aqueous solution as used in Example 1 was supplied at a rate of 10 kg/h to the 23rd plate from above of an azeotropic dehydration column provided with 50 sieve trays. It was distilled inn the azeotropic dehydration column under a column top absolute pressure of 173 hPa at the 14th plate temperature of 57° C. The column top gas was condensed in the condenser (9) attached to the column. When the toluene phase (4) obtained by separating the resultant condensate into two phases was wholly refluxed at a rate of 30 kg/h, the acrylic acid concentration of the column top gas was found to be 0.2 wt. % and the amount of steam supplied to the reboiler to be 12.7 kg/h. Incidentally, the reflux liquid had incorporated phenothiazine therein as a polymerization inhibitor till a concentration of 150 ppm and was distilled with molecular oxygen supplied thereto through the bottom of the column at a rate of 60 N liters/h.

The amount of the vapor in the azeotropic dehydration column was found to be 12.7 kg/h. The bottoms of the column had an acetic acid concentration of not more than 500 ppm and contained absolutely no toluene or water.

After this operation was continued under the conditions described above for 14 days, the interior of the column was inspected to find that a deposit had formed on the 23rd plate and absolutely no other abnormality had occurred.

What is claimed is:

1. A method for the production of acrylic acid, comprising a step of subjecting propylene and/or acrolein to a reaction of catalytic gas phase oxidation, a step of absorbing the acrylic acid contained in the gas formed by said reaction of catalytic gas phase oxidation with a absorbent, and a step of dehydrating the acrylic acid-containing aqueous solution obtained by said step of absorption, and characterized by said step of dehydration adding an azeotropic solvent capable of forming an azeotropic mixture with acetic acid and water and distilling the resultant mixture and adjusting the acrylic acid concentration at the top of said azeotropic dehydration column in the range of 0.06–0.80 wt. % thereby preventing the bottoms of said azeotropic dehydration column from substantially containing said azeotropic solvent and water.

2. A method according to claim 1, wherein the acrylic acid concentration in the acrylic acid-containing aqueous solution to be supplied to said step of dehydration is in the range of 55–80 wt. %.

3. A method according to claim 1, wherein said adjustment of the acrylic acid concentration at the top of said azeotropic dehydration column comprises having a condenser attached to said azeotropic dehydration column thereby obtaining a condensate containing at least acrylic acid, acetic acid, an azeotropic solvent, and water, separating said condensate into an azeotropic solvent-containing phase and a water phase, and subsequently refluxing said azeotropic solvent-containing phase to said azeotropic dehydration column.

4. A method according to claim 2, wherein said adjustment of the acrylic acid concentration at the top of said azeotropic dehydration column comprises having a condenser attached to said azeotropic dehydration column thereby obtaining a condensate containing at least acrylic acid, acetic acid, an azeotropic solvent, and water, separating said condensate into an azeotropic solvent-containing phase and a water phase, and subsequently refluxing said azeotropic solvent-containing phase to said azeotropic dehydration column.

5. A method according to claim 3, wherein the water phase of said condensate is reclaimed as an absorbent for use in said step of absorption.

6. A method according to claim 4, wherein the water phase of said condensate is reclaimed as an absorbent for use in said step of absorption.

7. A method according to claim 1, wherein the bottoms of said azeotropic dehydration column are further introduced to an acetic acid separation column and distilled to attain separation of acetic acid.

8. A method according to claim 7, wherein an acrylic acid-containing condensate is obtained from the top part of said acetic acid separation column and at least part thereof is supplied to said azeotropic dehydration column.

9. A method according to claim 8, wherein the position to which said acrylic acid-containing condensate is supplied is on the same level as the position at which said azeotropic dehydration column is supplied with said acrylic acid-containing aqueous solution or lower than said latter position.

\* \* \* \* \*